(12) United States Patent
Ouchi (10) Patent No.: US 6,210,398 B1
(45) Date of Patent: Apr. 3, 2001

(54) MANIPULATING PART OF ENDOSCOPIC TREATMENT TOOL

(75) Inventor: Teruo Ouchi, Saitama (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/321,133

(22) Filed: May 27, 1999

(30) Foreign Application Priority Data

May 28, 1998 (JP) .................................................. 10-146808

(51) Int. Cl.⁷ .................................................. A61B 17/00
(52) U.S. Cl. .................... 606/1; 606/205; 600/184
(58) Field of Search .............................. 606/1, 205, 167; 600/101, 184

(56) References Cited

U.S. PATENT DOCUMENTS

| | | | | |
|---|---|---|---|---|
| 5,376,094 | * | 12/1994 | Kline | 606/113 |
| 5,666,965 | * | 9/1997 | Bales et al. | 128/749 |
| 5,683,413 | * | 11/1997 | Miyagi | 606/205 |
| 5,766,184 | * | 6/1998 | Matsuno et al. | 606/142 |
| 5,843,091 | * | 12/1998 | Holsinger et al. | 606/108 |

* cited by examiner

*Primary Examiner*—Linda C. M. Dvorak
*Assistant Examiner*—Jocelyn Ram
(74) *Attorney, Agent, or Firm*—Greenblum & Bernstein, P.L.C.

(57) ABSTRACT

A manipulating part of an endoscopic treatment tool, in which, to a cylindrical member having a first finger retaining member, there is slidably mounted a second finger retaining member slidably for remotely driving a distal end operating part using a sliding movement of the second finger retaining member along the cylindrical member. For the manipulating part, a stopper is added, which is movably provided on the cylindrical member, and which is fixed at an arbitrary position on the cylindrical member. The stopper is designed to restrict a length of the sliding movement of the second finger retaining member.

4 Claims, 8 Drawing Sheets

MANIPULATING PART OF ENDOSCOPIC TREATMENT TOOL

BACKGROUND OF THE INVENTION

The present invention relates to a manipulating part of an endoscopic treatment tool that is to be inserted into a treatment tool insertion channel of an endoscope.

In general, an endoscopic treatment tool is designed such that a distal end operating section is driven with a manipulating part on an operator side through a manipulating wire passed through and axially movable with respect to a sheath inserted into a treatment tool insertion channel of an endoscope.

The manipulating part is generally equipped with a first finger retaining member that is attached to a cylindrical member connected to the proximal end of the sheath, and a second finger retaining member that is slidable relative to the cylindrical member and connected to the proximal end of the manipulating wire. The sliding motion of the second finger retaining member along the cylindrical member causes the axial motion of the manipulating wire.

In case of some treatment tools, such as an endoscopic forceps tool, which use a closely wound coil as the sheath, the manipulating stroke varies depending on the degree of bending of the sheath. Therefore, during the use of the tool, the manipulating stroke may be too short to perform sufficient operation, or excessively long, causing the buckling of the manipulating wire.

In case of a high frequency snare, a basket type grasping tool, etc. in which a plurality of elastically contractible and expandable wires are retracted into or protruded from the distal end of the sheath, the constant size of the expanded elastic wires is inconvenient for an operator to treat a polyp, a foreign matter or the like which has a different size.

SUMMARY OF THE INVENTION

Accordingly, an object of the present invention is to provide a manipulating part of an endoscopic treatment tool, which makes it possible to readily adjust the stroke of a manipulating wire depending on the condition of use.

To achieve the above-noted object, the present invention provides a manipulating part of an endoscopic treatment tool, comprising: a shaft member having a first finger retaining member; a second finger retaining member slidably mounted to the shaft member so that a sliding movement of the second finger retaining member along the shaft member drives a distal end operating part remote from the manipulating part; and a stopper movably provided on the shaft member, and fixed at an arbitrary position on the shaft member, the stopper restricting a length of the sliding movement of the second finger retaining member.

The stopper may be fixed by a manually-operable screw relative to the shaft member, or the shaft member may be elastically deformed to permit the movement of the stopper relative to the shaft member, while a deformation restricting member may be connected to the second finger retaining member to inhibit the elastic deformation of the shaft member when the second finger retaining member is located close to the stopper.

In the latter case, it is preferable that the stopper is annular and surrounds the shaft member, at least one protrusion is provided on an inner circumferential surface of the stopper and a plurality of recesses each for engagement with the protrusion are provided on an outer surface of the shaft member and arranged along the length of the shaft member with intervals.

The stopper and the shaft member may be fixed to each other through a ratchet.

The shaft member is preferably in the form of a cylindrical member.

The present disclosure relates to the subject matter contained in Japanese patent application No. Hei. 10-146808 (filed on May 28, 1998), which is expressly incorporated herein by reference in its entirety.

DESCRIPTION OF THE PREFERRED EMBODIMENT

Preferred embodiments of the present invention will now be described in detail with reference to the accompanying drawings.

Figure 2:
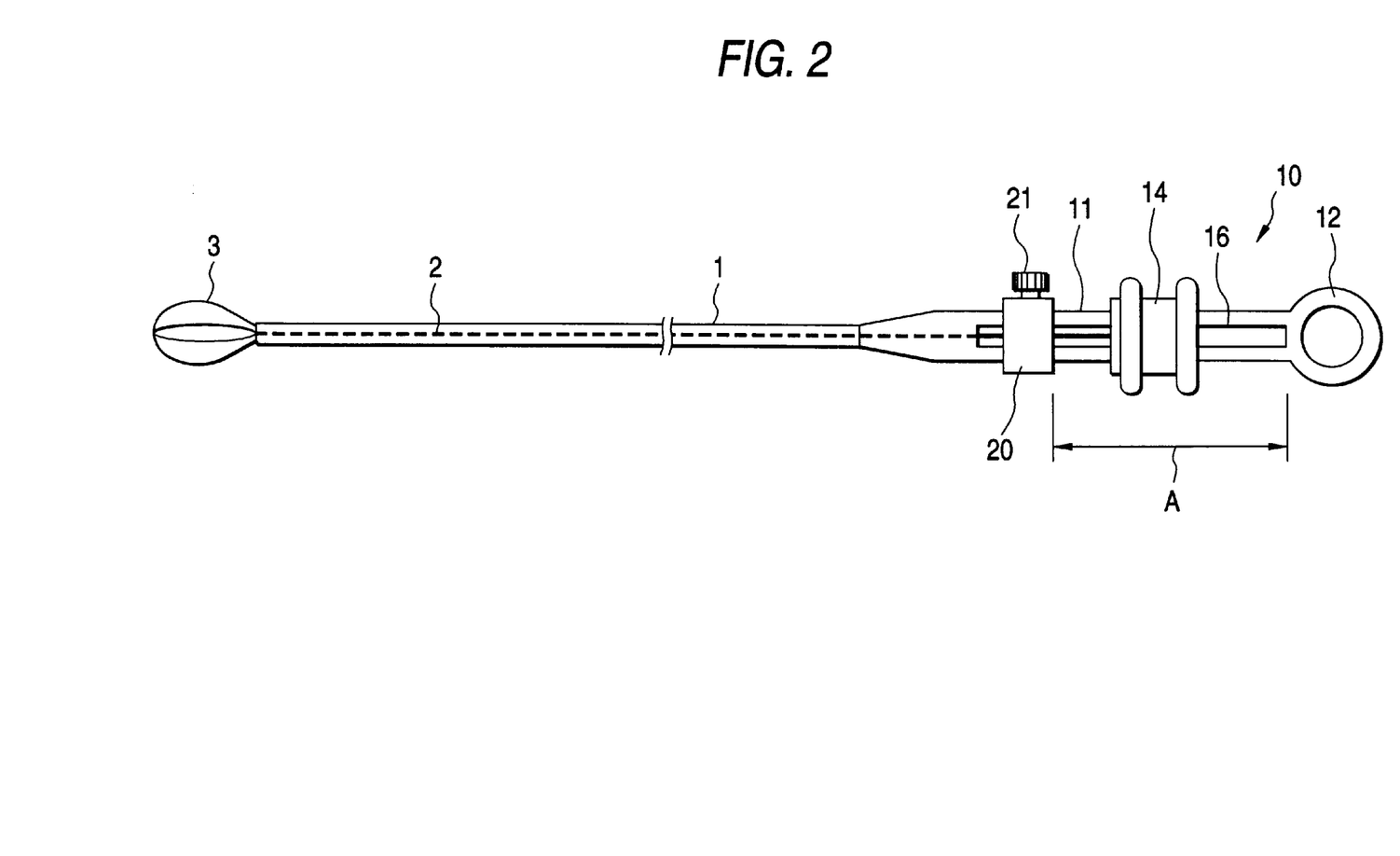
FIG. 2 is a plan view showing the entire construction of the endoscopic treatment tool according to the first embodiment.

FIG. 2 shows an endoscopic treatment tool according to a first embodiment of the present invention. As an example of the endoscopic treatment tools to which the present invention is applicable, a basket type grasping tool is illustrated. That is, the present invention is applicable not only to the basket type grasping tool but also to a high frequency snare, a biopsy forceps and other various endoscopic treatment tools.

Reference numeral 1 in the drawings denotes a flexible sheath adapted to be removably inserted into a treatment tool insertion channel of an endoscope, which is formed, for instance, of a resin tube made of tetrafluoroethylene. In addition, in case of the biopsy forceps, the sheath 1 is typically formed of a closely wound coiled wire.

A manipulating wire 2 is passed through the sheath 1 and axially movable relative thereto. A basket 3 constructed by a plurality of elastic wires is connected to the distal end of the manipulating wire 2 as a distal end operating part. The basket 3 is retracted into and protruded from the distal end of the sheath 1 by axially moving the manipulating wire 2.

The proximal end of the sheath 1 is connected to one end portion of a cylindrical (or rod-like) member 11 of a manipulating part 10 made of plastic material. The other end portion of the cylindrical member 11 is provided with an annular, first finger retaining member 12 for retaining operator's thumb thereon.

A spool-like, second finger retaining member 14 is axially-movably mounted on the cylindrical member 11 so as to receive operator's forefinger and middle finger thereon. The proximal end of the manipulating wire 2 is fixedly connected to the second finger retaining member 14.

By moving the second finger retaining member 14 along the cylindrical member 11, the manipulating wire 2 is axially moved within the sheath 1 to thereby expand or contract the basket 3 provided at the distal end.

Figure 1:
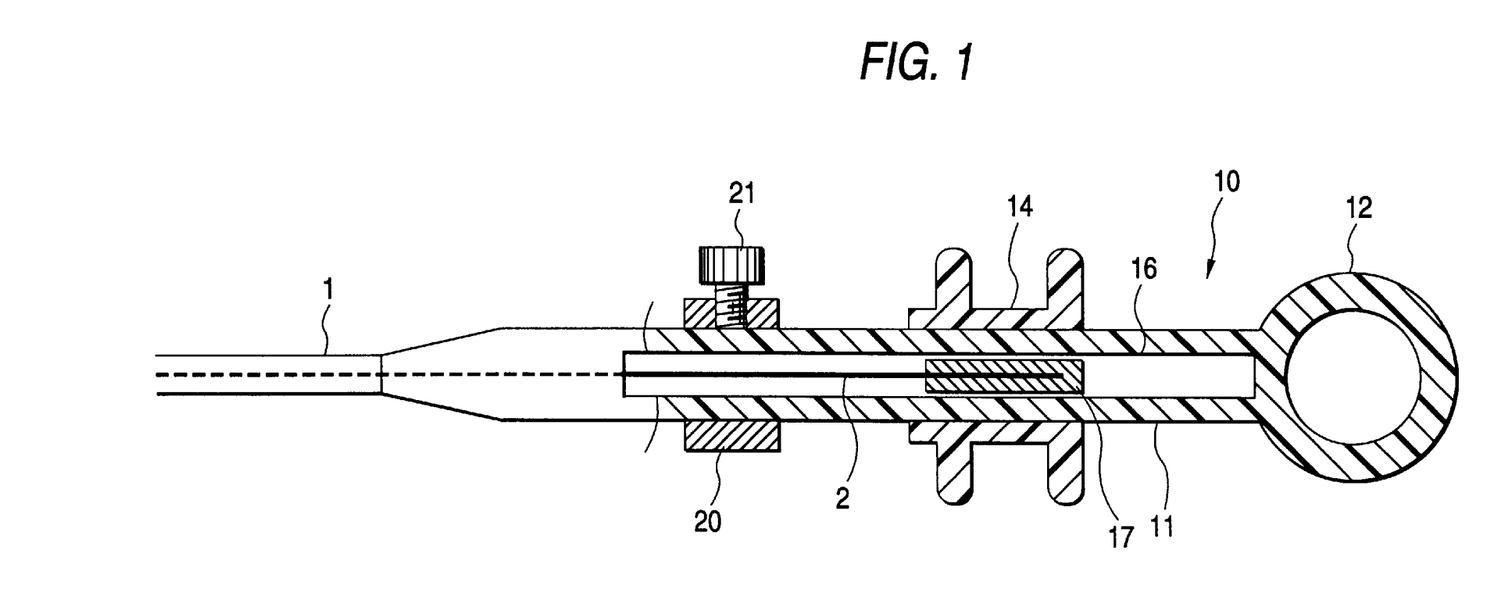
FIG. 1 is a sectional plan view showing a manipulating part of an endoscopic treatment tool according to a first embodiment of the present invention.

FIG. 1 is a sectional plan view of the manipulating part 10. The cylindrical member 11 is in the form of a slender circular column having a substantially constant outer diameter over the entire length thereof. A slit 16 having a constant width is formed through the cylindrical member 11 and elongated along the length of the cylindrical member 11.

Figure 3:
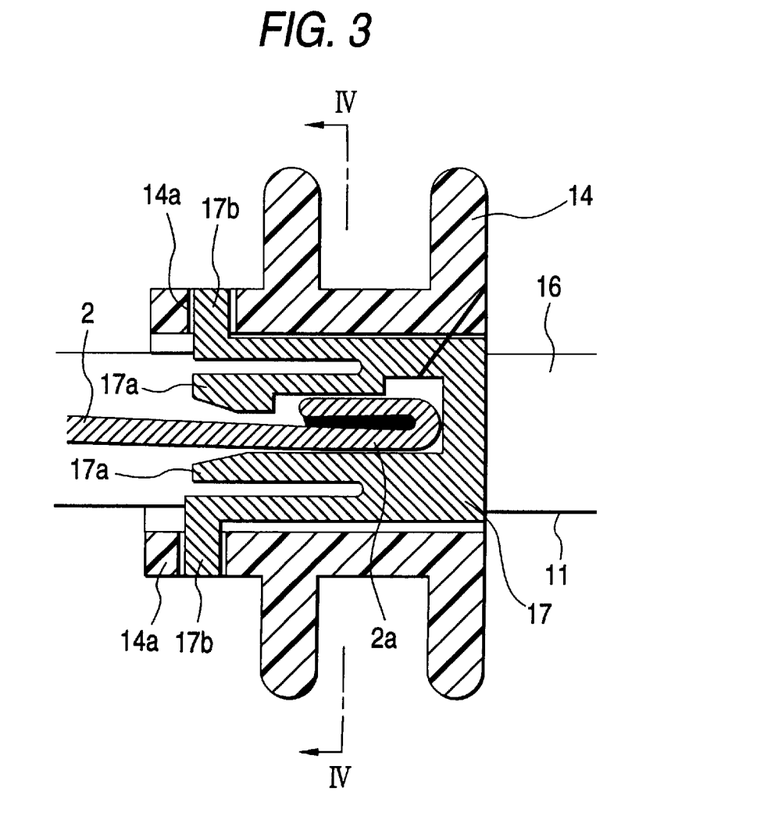
FIG. 3 is an enlarged, sectional side view showing a portion of the manipulating part of the endoscopic treatment tool according to the first embodiment.
Figure 4:
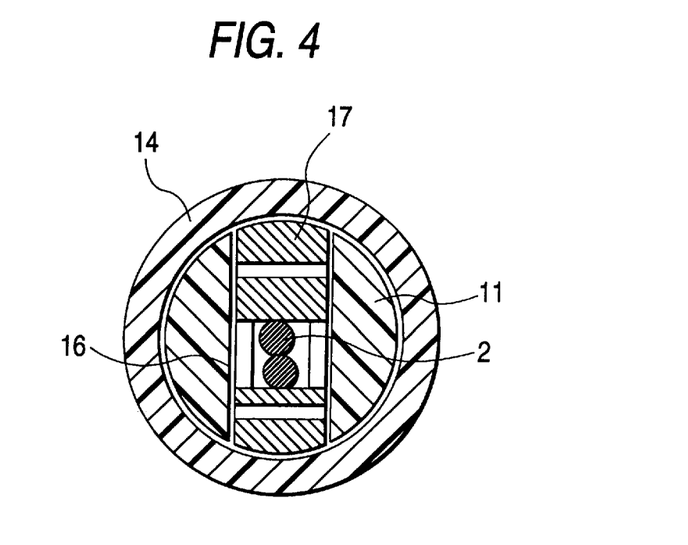
FIG. 4 is a sectional view taken along line IV—IV of FIG. 3.

A wire fixing member 17 is axially slidably disposed within the slit 16, and fixedly connects the proximal end of the manipulating wire 2 to the second finger retaining member 14. FIG. 3 is an enlarged sectional side view showing a manner of the connection by the wire fixing member 17, and FIG. 4 is a sectional view taken along line IV—IV of FIG. 3.

As illustrated, the wire fixing member 17 has a pair of elastically deformable, wire retaining arms 17a into which the proximal end 2a of the manipulating wire 2 bent to form a lump having a relatively large outer dimension is inserted forcibly, and a pair of elastically deformable, connecting protrusions 17b which are inserted into and engaged with respective engagement holes 14a formed in the second finger retaining member 14.

With this arrangement, the wire fixing member 17 onto which the proximal end of the manipulating wire 2 is retained is slid along with the second finger retaining member 14 relative to the cylindrical member 11, and thus the axial motion of the second finger retaining member 14 causes the axial motion of the manipulating wire 2.

As shown in FIG. 1, an annular stopper 20 is fitted on the outer peripheral surface of the cylindrical member 11 and located forwardly of the second finger retaining member 14. A manually-operable screw 21 is threadingly engaged with a threaded hole formed through the stopper 20. The screw 21 has a head portion in the form of a knob. The stopper 20 can be moved along the cylindrical member 11 when the screw 21 is loosened, and can be surely fixed at an arbitrary position on the cylindrical member 11 when the screw 21 is tightened.

As illustrated in FIG. 2, a range or distance A where the second finger retaining member 14 is movable is defined at a rear end side by the rear end of the slit 16 and at a front end side by the stopper 20. Accordingly, the stroke of the manipulating wire 2 can be readily adjusted to be suitable for the currently required condition of the tool. That is, the stopper 20 can be moved to and fixed at an arbitrary position to define an appropriate stroke of the manipulating wire.

Figure 5:
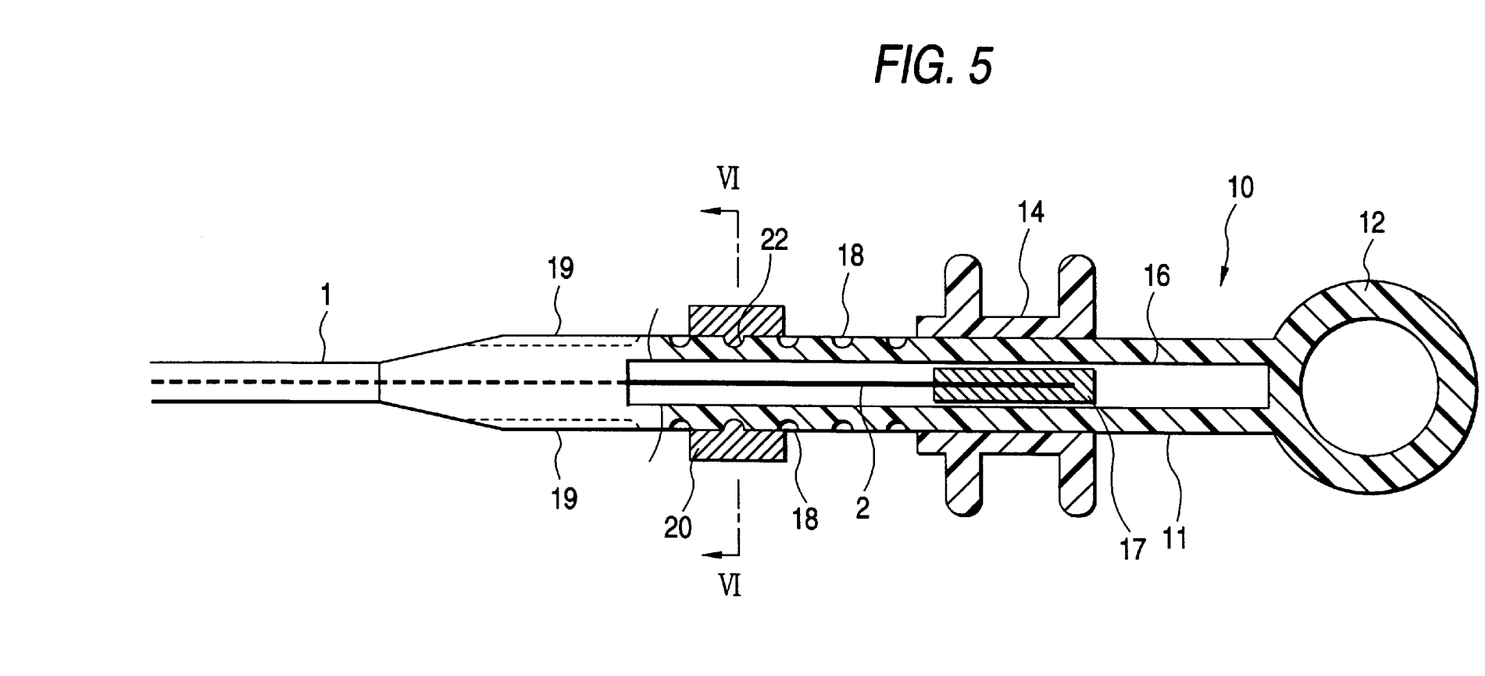
FIG. 5 is a sectional plan view showing a manipulating part of an endoscopic treatment tool according to a second embodiment of the present invention.

FIG. 5 shows a manipulating part 10 according to a second embodiment of the present invention. A structure for retaining the stopper 20 onto the cylindrical member 11 in the second embodiment is different from that in the first embodiment.

Figure 6:
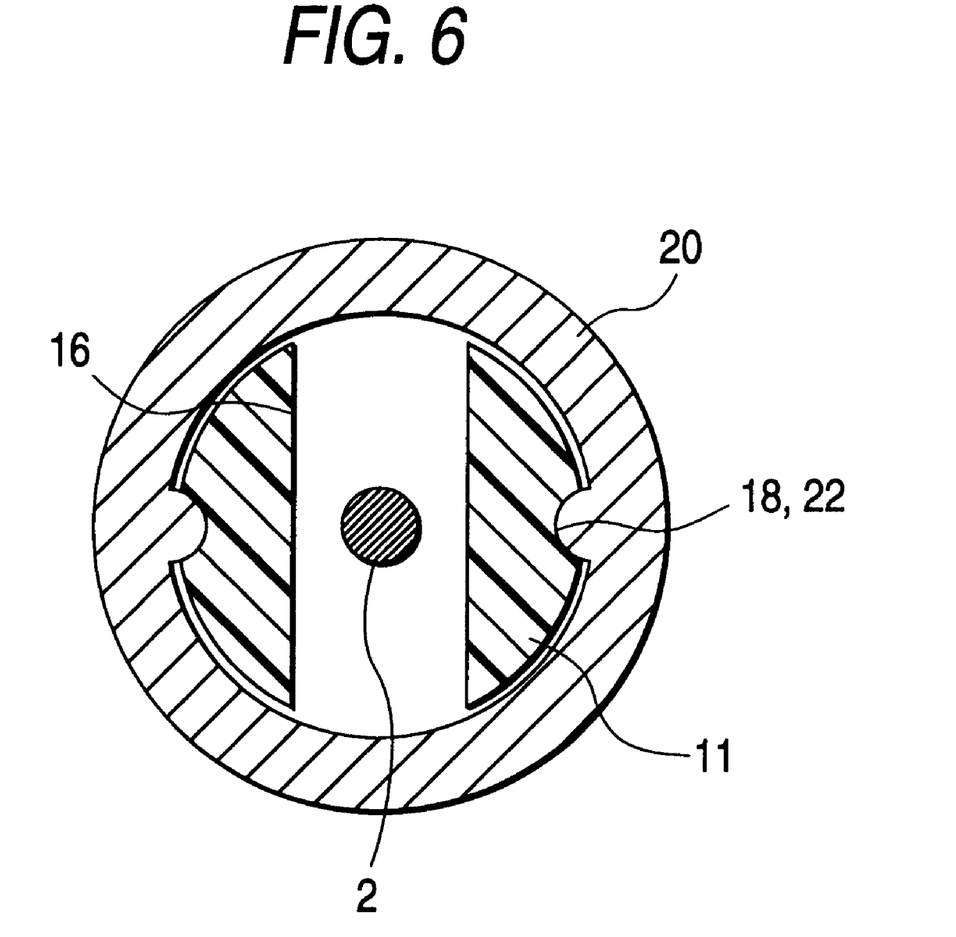
FIG. 6 is a sectional view taken along line VI—VI of FIG. 5.

As illustrated in FIG. 6 showing a cross-section taken along line VI—VI, a semi-spherical protrusion 22 is provided on the inner circumferential surface of the stopper 20 fitted on the cylindrical member 11. In this embodiment, a pair of semi-spherical protrusions 22 are provided at diametrically opposite positions, respectively.

A plurality of recesses (for example, about two to ten recesses) 18 are provided on the outer surface of the cylindrical member 11 along the length of the cylindrical member 11 at predetermined intervals, each for engagement with the protrusions 22 without rattling. Reference numeral 19 designates a guide groove along which the protrusion 22 is passed to be engaged with the recess 18 during assembly.

Figure 7:
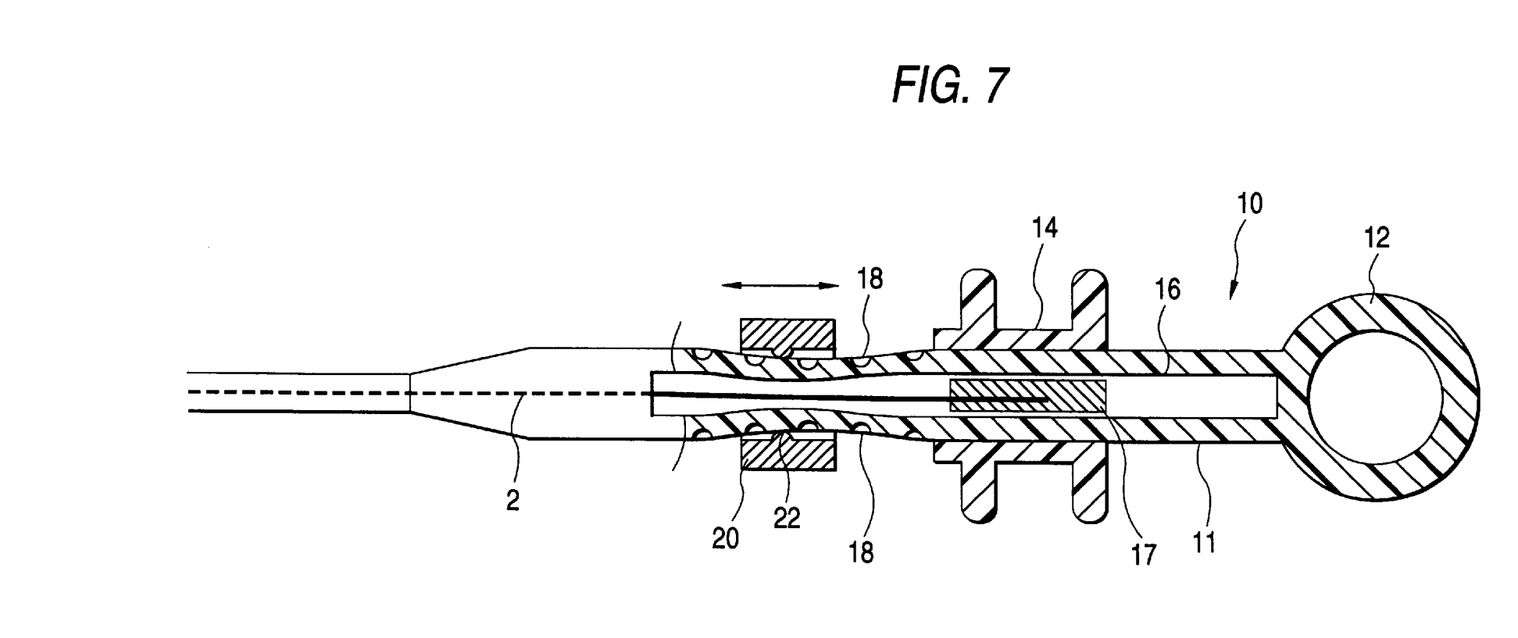
FIG. 7 is a sectional plan view showing a state in which a stopper position is being changed in the manipulating part of the endoscopic treatment tool according to the second embodiment.

The internal side of the cylindrical member 11 having the recesses 18 are formed with the slit 16 as previously described, and thus the spatial space of the slit 16 facilitates such flexibility of the cylindrical member 11 as shown in FIG. 7 that when a relatively strong axial force is applied to the stopper 20, the protrusion 22 is disengaged from the recess 18 while elastically deforming the cylindrical member 11 radially inwardly, and the stopper 20 is axially moved to engage the protrusion 22 with desired another recess 18.

Figure 8:
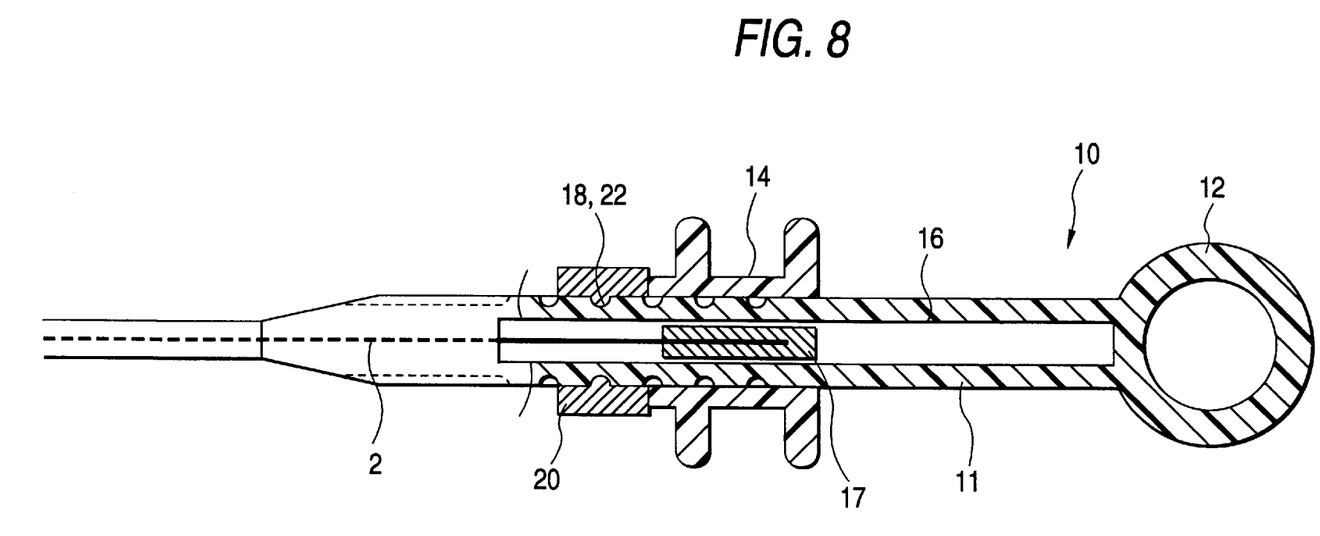
FIG. 8 is a sectional plan view showing a state in which the stopper is in contact with a second finger retaining member in the manipulating part of the endoscopic treatment tool according to the second embodiment.

Note that since the slit 16 is substantially filled by the wire fixing member 17 and forms a deformation restricting member at a position where the second finger retaining member 14 is fitted on the outside of the cylindrical member 11, the cylindrical member 11 cannot be deformed to disengage the protrusion 22 of the stopper 20 from the recess 18 when the second finger retaining member 14 is moved forwardly and contacted with the stopper 20.

Therefore, a range or distance where the second finger retaining member 14 is movable forwardly is defined by the stopper 20. Accordingly, the stroke of the manipulating wire 2 can be readily adjusted to be suitable for the currently required condition of the tool. That is, an appropriate stroke of the manipulating wire can be defined by simply selecting one of the recesses 18 to be engaged with the protrusion 22 of the stopper 20.

Figure 9:
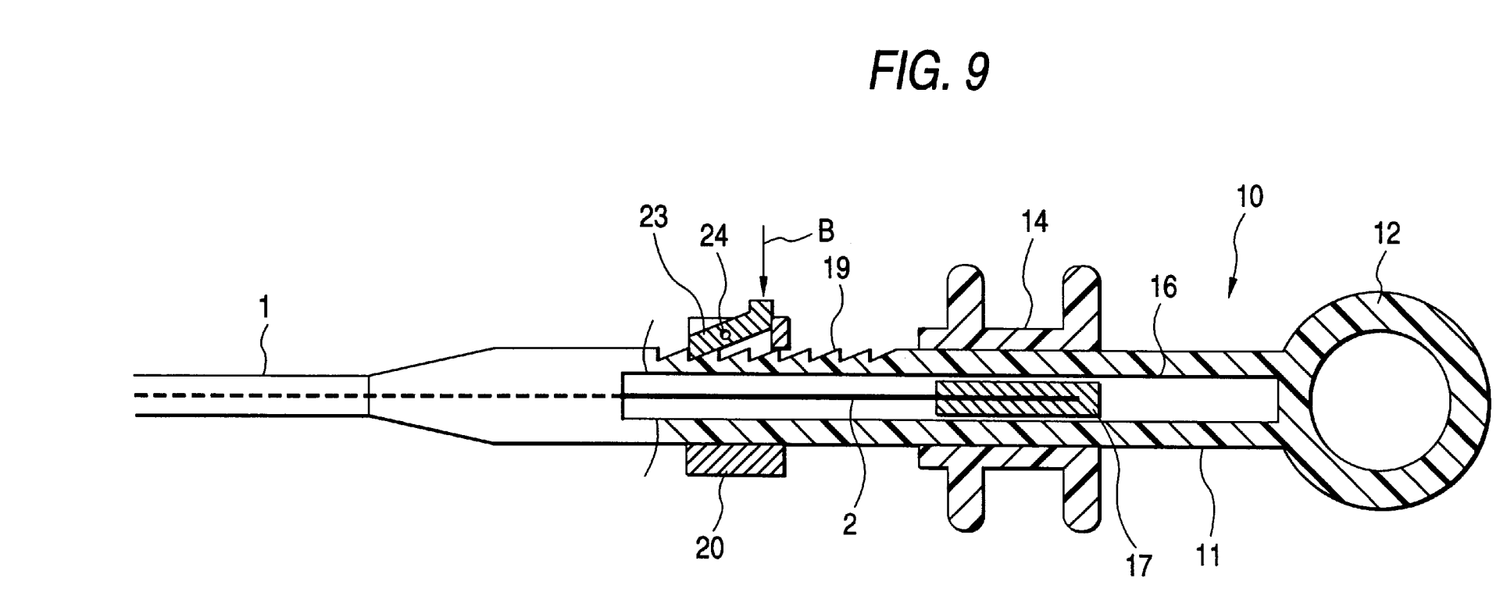
FIG. 9 is a sectional plan view showing a manipulating part of an endoscopic treatment tool according to a third embodiment of the present invention.

FIG. 9 shows an manipulating part 10 according to a third embodiment of the present invention. A structure for retaining the stopper 20 onto the cylindrical member 11 in the third embodiment is different from those in the first and second embodiments.

In this embodiment, a plurality of ratchet grooves 19 are formed on the outer circumferential surface of the cylindrical member 11, whereas a ratchet claw 23 is formed on the stopper 20 for engagement with selected one of the ratchet grooves 19 to inhibit the forward movement of the stopper 20 relative to the cylindrical member 11.

The ratchet claw 23 is mounted on the stopper 20 so as to be rotatable about the axis 24. Therefore, by pushing the rear end portion of the ratchet claw 23 in a direction indicated by an arrow B, the engagement between the front end portion of the ratchet claw 23 and the ratchet groove 19 can be released. Upon the disengagement of the ratchet claw 23 from the ratchet groove 19 the stopper 20 is moved to an arbitrary position, and then the ratchet claw 23 is again engaged with another ratchet groove 19 at that position to adjust the stroke of the manipulating wire 2.

In addition, the present invention should not be limited to the embodiments described above. The movable stopper 20 may be provided behind the second finger retaining member 14, or two movable stoppers 20 may be respectively provided forwardly and behind the second finger retaining member 14. The configuration of the stopper 20 and the structure for engaging/disengaging the stopper 20 with/from the cylindrical member 11 may be modified in any suitable ways.

According to the present invention, a stopper for restricting a slidable range in which a second finger retaining member is slidable is provided on a cylindrical member of a manipulating part so that the stopper can be fixed at an arbitrary position. Therefore, a stroke of a manipulating wire can be readily adjusted depending on the condition or situation. That is, it is possible to eliminate the insufficiency or excessiveness of the manipulating stroke which may hinder an appropriate operation or cause the buckling of the manipulating wire. In case of a treatment tool having an expandable and contractible distal end operating part, the stroke can be adjusted to an optimum one appropriate for the size of a polyp, a foreign matter, etc. to ensure the speedy and positive treatment.

What is claimed is:

1. A manipulating part of an endoscopic treatment tool, comprising:

a shaft member having a first finger retaining member and an elongated slit formed along the length of said shaft member;

a second finger retaining member slidably mounted to said shaft member so that a sliding movement of said second finger retaining member along said shaft member drives a distal end operating part remote from said manipulating part; and a stopper movably provided on said shaft member, and fixed at an arbitrary position on said shaft member and along the length of said slit, said stopper restricting a length of said sliding movement of said second finger retaining member;

wherein said shaft member is elastically deformed along the length of said slit to permit said movement of said stopper relative to said shaft member, and a deformation restricting member is connected to said second finger retaining member in said elongated slit to inhibit said elastic deformation of said shaft member when said second finger retaining member is located close to said stopper.

2. The manipulating part according to claim 1, wherein said stopper is annular and surrounds said shaft member, at least one protrusion is provided on an inner circumferential surface of said stopper and a plurality of recesses each for engagement with said protrusion are provided on an outer surface of said shaft member and arranged along the length of said slit at predetermined intervals.

3. The manipulating part according to claim 1, wherein said shaft member is cylindrical.

4. A manipulating part of an endoscopic treatment tool, comprising:

a shaft member having a first finger retaining member;

a second finger retaining member slidably mounted to said shaft member so that a sliding movement of said second finger retaining member along said shaft member drives a distal end operating part remote from said manipulating part; and a stopper movably provided on said shaft member, and fixed at an arbitrary position on said shaft member, said stopper restricting a length of said sliding movement of said second finger retaining member, said stopper including a manually-operable screw extending transversely to an axis of said shaft member, whereby said screw is tightened against an outer surface of said shaft member to fix said stopper at said arbitrary position.

* * * * *

UNITED STATES PATENT AND TRADEMARK OFFICE
CERTIFICATE OF CORRECTION

PATENT NO. : 6,210,398 B1
DATED : April 3, 2001
INVENTOR(S) : T. Ouchi

It is certified that error appears in the above-identified patent and that said Letters Patent is hereby corrected as shown below:

<u>Title page,</u>
Item [56], References Cited, the following U.S. PATENT DOCUMENTS, were omitted and should be inserted:
-- 4,655,219      4/1987      Petruzzi
   4,178,810      12/1979     Takahashi
   5,882,293      3/1999      Ouchi --
The following FOREIGN PATENT DOCUMENTS was omitted and should be inserted:
-- 57-40964       9/1982      Japan --

Signed and Sealed this

Thirty-first Day of December, 2002

JAMES E. ROGAN
*Director of the United States Patent and Trademark Office*